United States Patent [19]

Holtkamp, Sr.

[11] Patent Number: Plant 6,310

[45] Date of Patent: Sep. 27, 1988

[54] AFRICAN VIOLET PLANT NAMED SEATTLE

[75] Inventor: Reinhold Holtkamp, Sr., Isselburg, Fed. Rep. of Germany

[73] Assignee: Optimara Erfinder Gemeinschaft, Rees Haffen, Fed. Rep. of Germany

[21] Appl. No.: 823,519

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Seattle having single, star-shaped light pink flowers; prominent bright yellow anthers; girl-type leaves; early and profuse flowering; vigorous growth habit, and strong and upright flower stems which carry the long-lasting and non-dropping flowers in a tight flower head above the foliage.

1 Drawing Sheet

The present invention comprises a new and distinct cultivar of African violet plant, botanically known as *Saintpaulia ionantha*, and hereinafter referred to by the cultivar name Seattle.

The new cultivar was originated from a cross made in a controlled breeding program in Isselburg, West Germany. The female, or seed parent was a cultivar designated 349 light pink girl. The male, or pollen parent was a cultivar designated 68 red single. The new cultivar was given the breeding number H40/IV.

Seattle was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Seattle has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Seattle, which in combination distinguish this African violet as a new and distinct cultivar:

1. Light pink star-shaped flowers combine with bright yellow anther cells to provide attractive flowers; surfaces of petals have a crystal-like sparkle.
2. Strong upright flower stems.
3. First flash of flowers form a tight bouquet above the leaves.
4. Profuse flowering.
5. Long-lasting, non-dropping single flowers.
6. Each plant carries up to 7 to 9 and more upright flower stems, each of which carries 6 and more flowers.
7. Plant saleable 8 to 9 weeks after potting.
8. Girl-type medium to dark green velvet leaves with bright green centers.
9. Vigorous grower.
10. Seed capsule pushes slightly through.

The accompanying photographic drawing shows a typical specimen plant of the new cultivar grown in a 10 cm. pot. The colors appearing in the photograph are as true as possible with color illustrations of this type. Under cooler growing conditions or more intensive lighting, the pink flower color will intensify.

In the following description, color references are made to The Royal Horticultural Society Colour Chart (R.H.S.), except where general colors of ordinary significance are referred to. Color values were taken under natural light conditions at approximately 1:00 p.m. in Nashville, Tenn.

Botanical classification: *Saintpaulia ionantha*, Ramat., cv. Seattle.

Parentage:

*Male parent.*—68 red single.

*Female parent.*—349 light pink girl.

Propagation: The new cultivar holds its distinguishing characteristics through successive propagations by leaf cuttings.

PLANT

From 8 cm. to 10 cm. tall when grown in pots, and approximately 24–27 cm. in diameter when fully grown.

Leaves:

*Shape.*—Round, girl-type with light green centers; edges highly serrated.

*Diameter.*—Approximately 70 mm.

*Texture.*—Velvety, hairy.

*Ribs and veins.*—Well pronounced on underside, light green and shiny; more purplish between the veins.

*Color (upper side).*—147A.

*Color (under side).*—148D.

*Petioles.*—Strong and sturdy; hairy, brownish green.

Flowers:

*Buds.*—Size: 8–10 mm. before opening. Shape: Ball-shaped.

*Sepals.*—Shape: Spear-shaped, hairy; five in number. Color: Dark brown.

*Calyx.*—Basifixed.

*Peduncle.*—Character: Strong, upright, hairy. Color: Brownish.

Individual flowers:

*Size.*—Approximately 40 mm.

*Shape.*—Single, star-shaped, slightly waved.

*Color (upper side).*—Approximately 65D, although precise color value is difficult to ascertain.

*Color (under side).*—69C-D.

*Borne.*—On flower stems which carry 7 and more flowers on strong, upright peduncles.

Flowering habit: Flowers 8 to 9 weeks after potting of small plantlets; compact flower head positioned above foliage; flowers are long-lasting and non-dropping.

Reproductive organs:

*Stamens.*—Five in number.

*Anthers.*—Five with two anther cells; bright yellow.

*Filaments.*—Bright green, 5 mm.

*Styles.*—6 mm., light purple.

Roots: Normally developed, white when young, turning slightly brownish when older.

Disease resistance: Good.

I claim:

1. A new and distinct cultivar of African violet named Seattle, as illustrated and described, and particularly characterized by its single, star-shaped light pink flowers; prominent bright yellow anthers; girl-type leaves; early and profuse flowering; vigorous growth habit; and by its strong and upright flower stems which carry the long-lasting and non-dropping flowers in a tight flower head above the foliage.

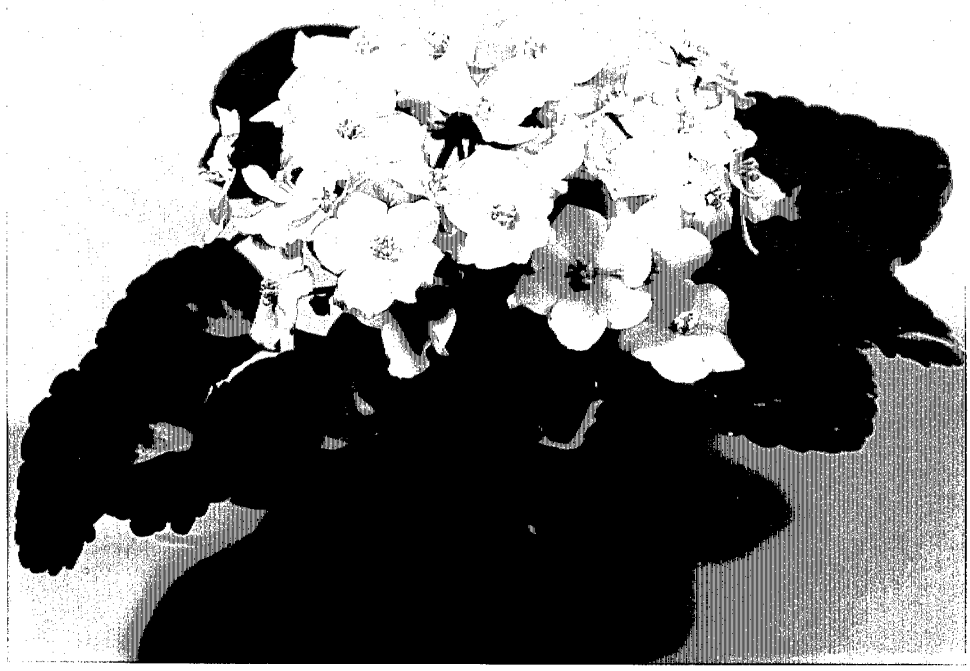

* * * * *